(12) United States Patent
Siess

(10) Patent No.: US 8,814,933 B2
(45) Date of Patent: Aug. 26, 2014

(54) FOLDABLE INTRAVASCULARLY INSERTED BLOOD PUMP

(75) Inventor: Thorsten Siess, Wuerselen (DE)

(73) Assignee: Abiomed Europe GmbH, Aachen (DE)

( * ) Notice: Subject to any disclaimer, the term of this patent is extended or adjusted under 35 U.S.C. 154(b) by 1679 days.

(21) Appl. No.: 11/667,258

(22) PCT Filed: Sep. 26, 2005

(86) PCT No.: PCT/EP2005/054804
§ 371 (c)(1),
(2), (4) Date: May 7, 2007

(87) PCT Pub. No.: WO2006/051023
PCT Pub. Date: May 18, 2006

(65) Prior Publication Data
US 2008/0103591 A1    May 1, 2008

(30) Foreign Application Priority Data
Nov. 12, 2004 (DE) .......... 10 2004 054 714

(51) Int. Cl.
*A61M 1/10* (2006.01)
*A61M 1/12* (2006.01)
(52) U.S. Cl.
CPC ............ *A61M 1/101* (2013.01); *A61M 1/1034* (2013.01); *A61M 1/125* (2013.01); *A61M 1/1024* (2013.01)
USPC ........................................ 623/3.13

(58) Field of Classification Search
CPC ... A61M 1/101; A61M 1/125; A61M 1/1034; A61M 1/1024; A61M 1/1036; A61M 1/1037; A61M 1/1039; A61M 1/1041; A61M 1/10
USPC ........ 600/16–18; 604/131, 151–153; 623/3.1, 623/3.13–3.15, 3.24–3.25
See application file for complete search history.

(56) References Cited

U.S. PATENT DOCUMENTS

| 4,753,221 A * | 6/1988 | Kensey et al. .................. 600/16 |
| 4,919,647 A * | 4/1990 | Nash ............................... 600/16 |
| 5,749,855 A * | 5/1998 | Reitan ........................... 604/151 |
| 6,217,541 B1 | 4/2001 | Yu |
| 6,533,716 B1 * | 3/2003 | Schmitz-Rode et al. ....... 600/16 |

FOREIGN PATENT DOCUMENTS

| WO | WO 94/05347 | 3/1994 |
| WO | WO 99/44651 | 9/1999 |

* cited by examiner

*Primary Examiner* — Carl H Layno
*Assistant Examiner* — Jessica Anthony
(74) *Attorney, Agent, or Firm* — Fulwider Patton LLP

(57) ABSTRACT

A foldable intravascularly insertable blood pump employs an impeller with radially delivering vanes in combination with an annular deflection channel. The impeller is driven by a shaft extending through a catheter wherein the impeller and its envelope are foldable by relative displacement of the shaft and catheter.

14 Claims, 7 Drawing Sheets

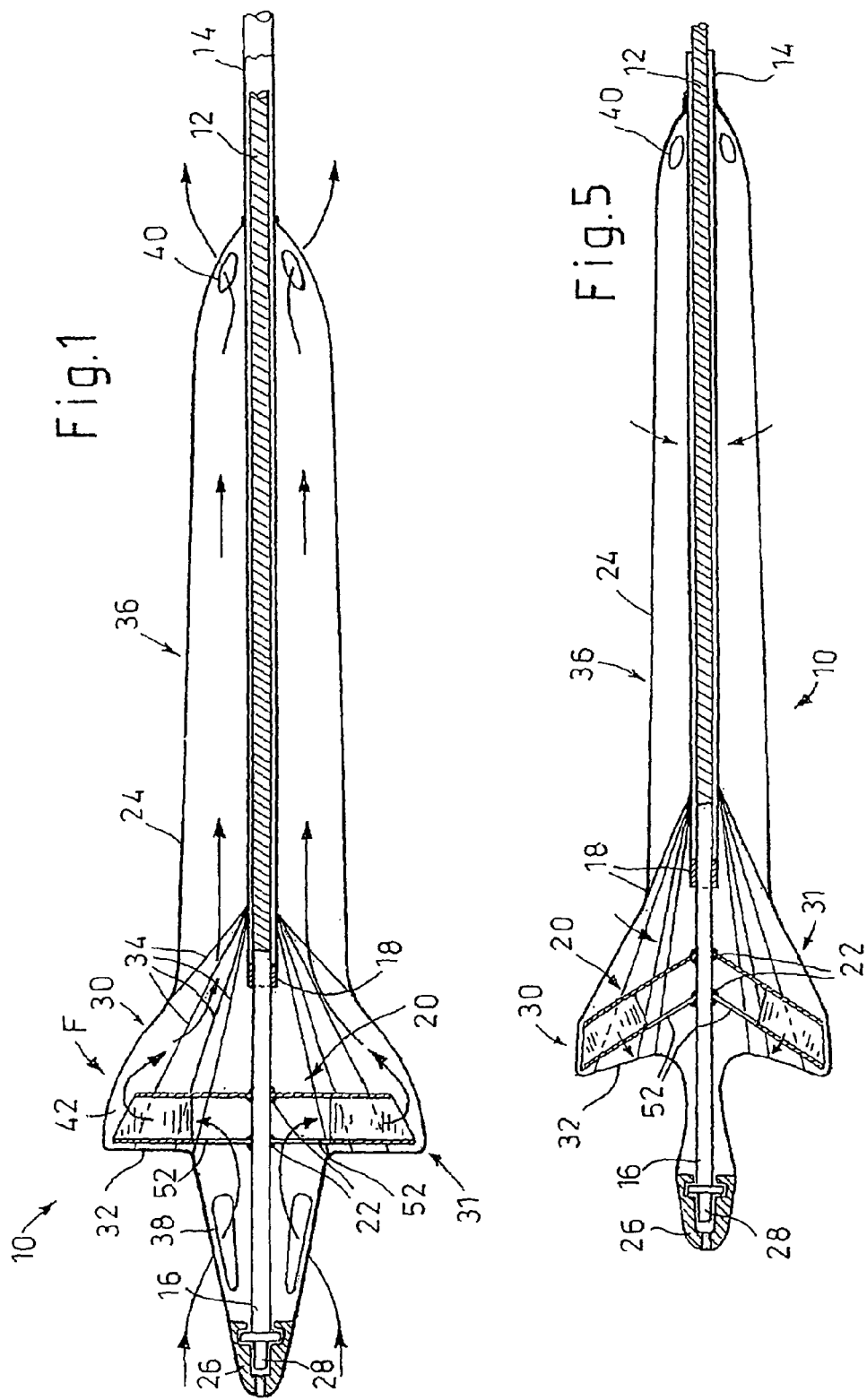

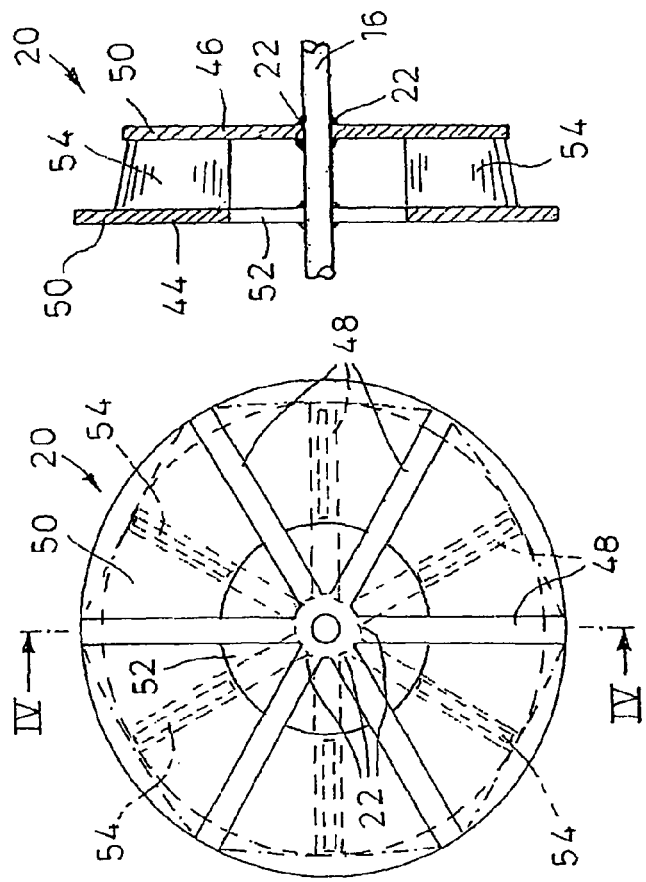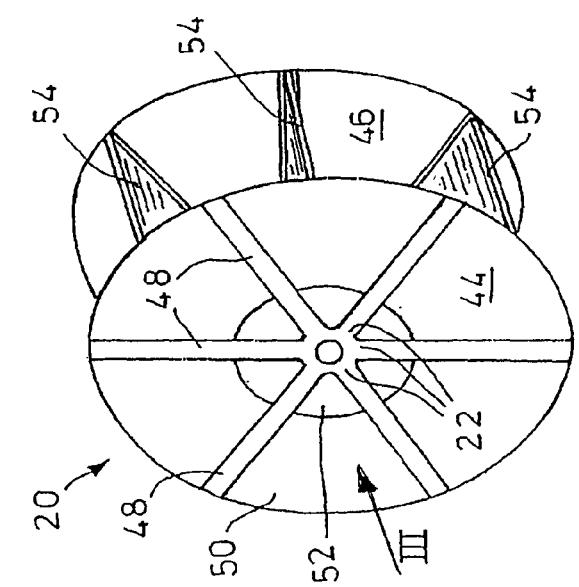

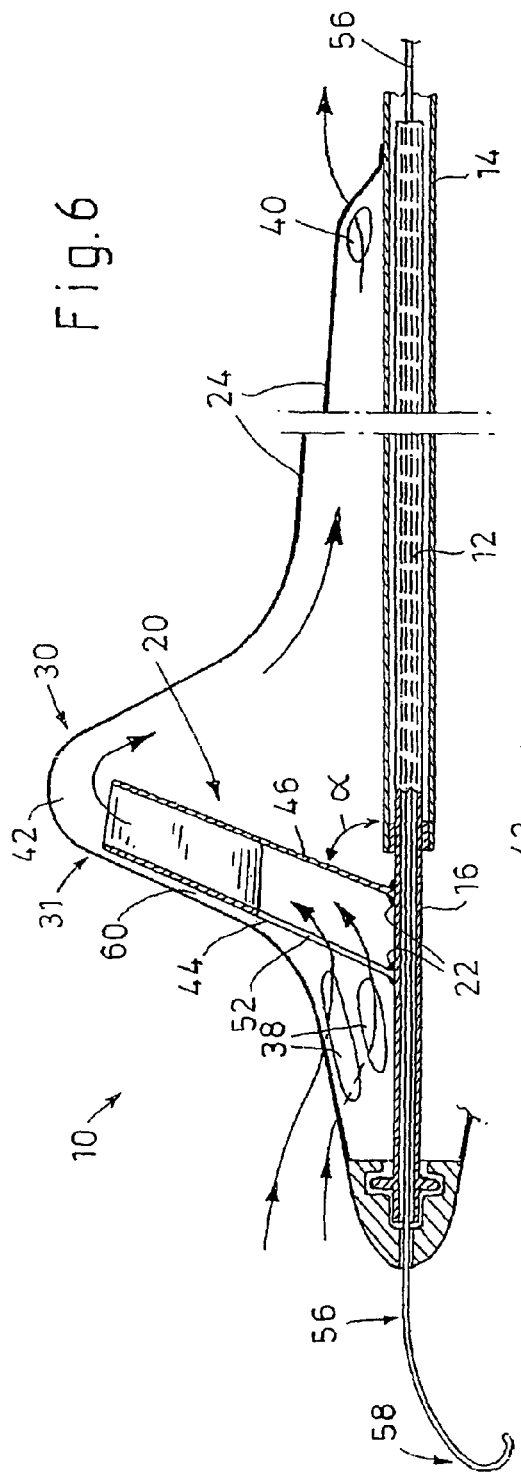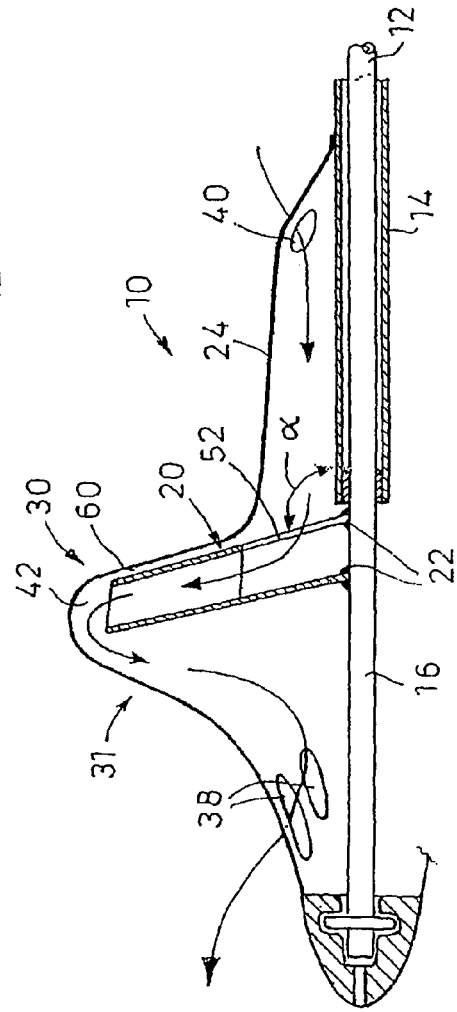

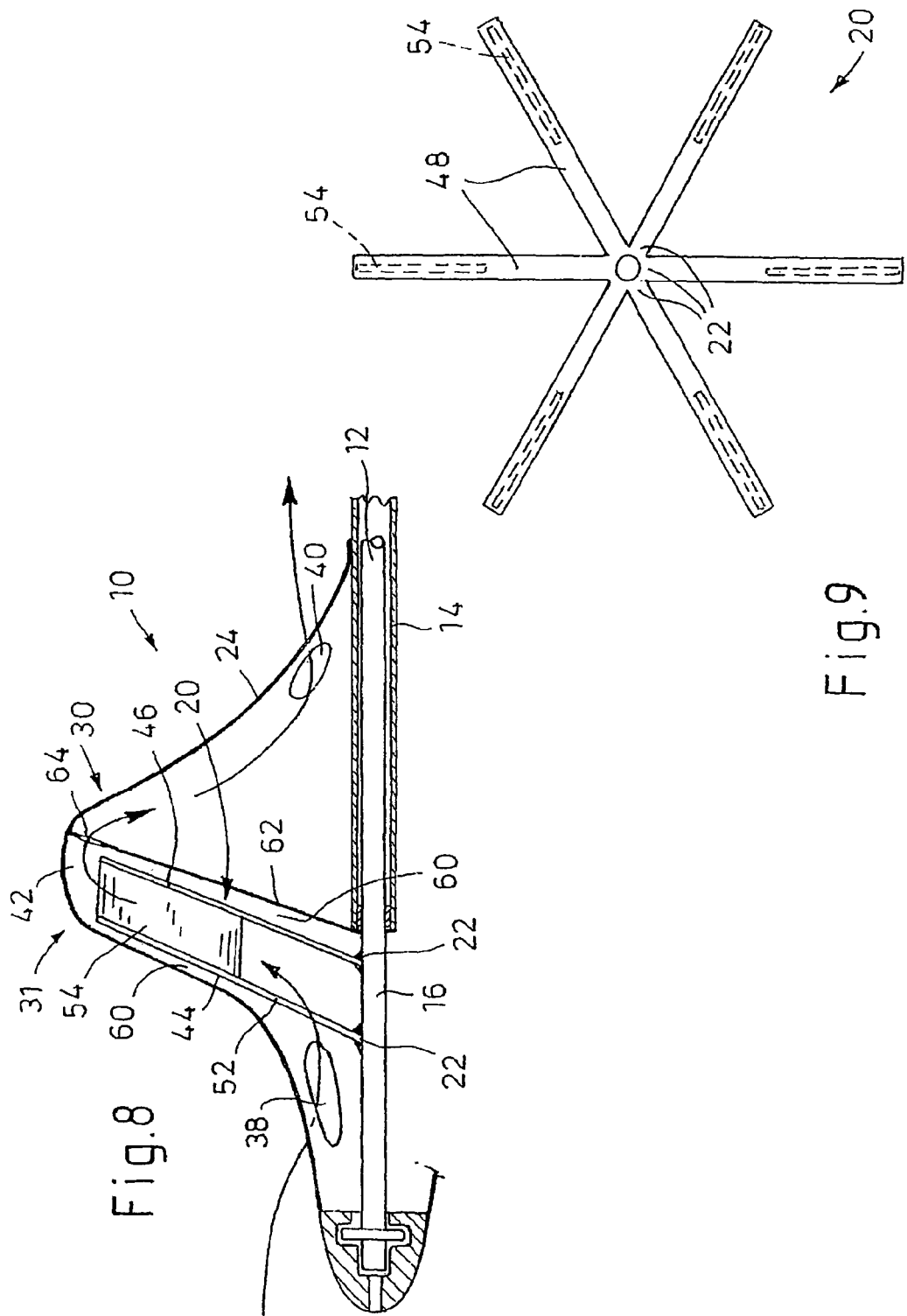

FOLDABLE INTRAVASCULARLY INSERTED BLOOD PUMP

RELATED APPLICATIONS

This application is a U.S. national phase of PCT/EP05/054804, filed Sep. 26, 2005, which claims priority from German Application No. 102004054714.9, filed Nov. 12, 2004.

BACKGROUND OF THE INVENTION

1. Field of the Invention

The invention relates to a foldable intravascularly insertable blood pump comprising a rotor provided with vanes, a flexible shaft extending through a catheter and adapted to drive the impeller, and an envelope enclosing the impeller.

2. Description of Related Art

Rotary blood pumps are known which are inserted into the heart for supporting the pumping capacity of the natural heart. Insertion is performed intravascularly, namely through the blood vessel system of the patient. It is thus required that, upon insertion, the maximum diameter of the blood pump does not exceed 3 mm, if the insertion is to be carried out through an insertable tube and with as little complication as possible. Further, the blood pump should be flexible for the purpose of conforming to the bends of the vessel course.

An intravascularly insertable flexible blood pump which forms the basis of the first part of claim 1 is described in WO 99/44651. The blood pump is a self-unfolding pump and comprises a flexible compressible envelope in the form of a tube which defines the pump housing. In the envelope a radially compressible rotor is arranged. The rotor is configured as a helix driving the blood flow in axial direction. The drive shaft of the rotor extends through a catheter. The catheter, together with the housing and the rotor, can be drawn into a tube sleeve. In such an axial pump the requirements concerning dimensional accuracy of the axial pump are relatively high. The rotor must conform, within close tolerances, to the inner shape of the housing for the purpose of attaining a flow rate of at least 2 l/min. (liters per minute) at physiological pressure conditions and without excessively destroying blood. These requirements are difficult to fulfill with a foldable blood pump. The axial pump must be operated at a relatively high speed of 30,000 to 35,000 rpm.

SUMMARY OF THE INVENTION

It is an object of the invention to provide a foldable intravascularly insertable blood pump of simplified configuration and reduced susceptibility to failure. According to the invention, the rotor is a radially delivering impeller. The envelope comprises an annular bulge in the impeller region, wherein between the radially outer ends of the vanes and the envelope an annular deflection channel is defined which deflects the radial blood flow in axial direction. The blood pump according to the invention is a centrifugal pump, wherein the impeller accelerates the liquid in a radial outward direction without any essential axial component. Such a centrifugal pump does not require close tolerances between the impeller and the envelope. The axial alignment of the flow is produced by deflection. The blood pump is unsusceptible to misalignments and allows for large tolerances, which is of great importance in particular in a foldable pump. A radially delivering impeller requires a relatively low speed of approximately 5,000 to 15,000 rpm for radially delivering a typical amount of blood of approximately 2 to 5 l/min. The technical setup of the radial pump is simple.

The impeller and the envelope can be folded by relative displacement of the shaft and the catheter. The folding and unfolding processes may be actively initiated e.g. by a surgeon or cardiologist.

The impeller may comprise two essentially parallel supporting walls between which flexible sails are provided as vanes. This offers a technically simple configuration of a foldable impeller and thus the required stability when the impeller rotates for the purpose of delivering blood. For further increasing the stability, at least one of the supporting walls may be provided with spokes. The spokes may be radially arranged and, together with the impeller, are adapted to be folded against the shaft.

One supporting wall may be of continuous configuration, i.e. extending radially continuously from the shaft to the radially outer end of the supporting wall, and the other supporting wall may comprise an opening enclosing the shaft. The continuous supporting wall is preferably the rear supporting wall as seen in the direction of blood flow, and the supporting wall comprising the opening is preferably the front supporting wall as seen in the direction of blood flow. The blood may flow in though the supporting wall comprising the opening, and is then deflected towards the vanes by the continuous supporting wall. This allows a simple manner of deflecting an axial blood flow for the purpose of radial delivery.

The supporting walls may be fastened to the shaft by hinges. This allows the supporting walls to be folded against the shaft for reducing the outer diameter of the blood pump, for example for intravascular insertion of the pump. The effect of the centrifugal force produced during rotation of the shaft lends to the impeller the stability required for blood delivery.

Both supporting walls may be provided with spokes which are offset relative to each other such that the spokes are arranged side by side along the circumference of the shaft when the impeller is folded against the shaft. Thus the outer diameter of the blood pump is small in the folded condition.

Both supporting walls may comprise congruent spokes. The spokes preferably define spoke wheels, wherein between the respective congruent spokes of the two spoke wheels flexible sails may be arranged. The sails extend through the congruent arrangement of the spokes and perpendicularly to the plane of the spoke wheel. This arrangement allows for a simple technical setup of the impeller. At the front end the shaft may comprise a rigid portion to which the impeller is fastened for increasing the dimensional stability of the blood pump.

The envelope may comprise a cylindrical extension at end of which flow openings are provided. Preferably, the blood may leave the blood pump via the flow openings, and/or during operation of the blood pump in the opposite direction the blood may enter into the blood pump via the flow openings. The envelope may comprise a hub, e.g. at the end opposite to the cylindrical extension, in which hub the shaft is supported in an axially non-displaceable manner. In this case, the envelope is fastened to the shaft in a manner secured against rotation with the shaft.

The envelope may comprise a concentric planar wall arranged at a small distance to the impeller. Preferably, the concentric planar wall is disposed in front of the impeller as seen in the direction of blood flow. The small distance to the impeller results in only a small undesired return flow of blood between the impeller and the envelope. The concentric planar wall preferably comprises an opening enclosing the shaft, through which opening the blood can enter into the impeller.

The impeller may be adapted to be folded down in two opposite directions and axially to the shaft. On one side of the impeller the envelope may comprise a partition wall provided with a through-going opening in the region of the deflection channel. The partition wall may radially deflect the blood flow axially entering into the blood pump towards the vanes of the impeller. The blood delivered by the vanes may flow out through the through-going opening.

BRIEF DESCRIPTION OF THE DRAWINGS

Embodiments of the invention will now be described in greater detail with reference to the drawings in which:

FIG. 1 shows a lateral sectional view of a foldable intravascularly insertable blood pump, FIG. 2 shows a perspective view of the impeller of FIG. 1, FIG. 3 shows a view as seen in the direction indicated by arrow III of FIG. 2, FIG. 4 shows a sectional view taken along line IV-IV of FIG. 3, FIG. 5 shows the blood pump of FIG. 1 in partly folded condition, FIG. 6 shows a lateral sectional view of an embodiment of the blood pump with raised impeller, FIG. 7 shows a lateral sectional view of an embodiment of the blood pump with the impeller raised in the direction opposite to that shown in FIG. 6 and with opposite delivering direction, FIG. 8 shows a lateral sectional view of an embodiment of the blood pump comprising an additional partition wall behind the impeller, FIG. 9 shows a top view of the impeller of the embodiment shown in FIG. 8.

DETAILED DESCRIPTION OF THE PREFERRED EMBODIMENTS

Figure 10:
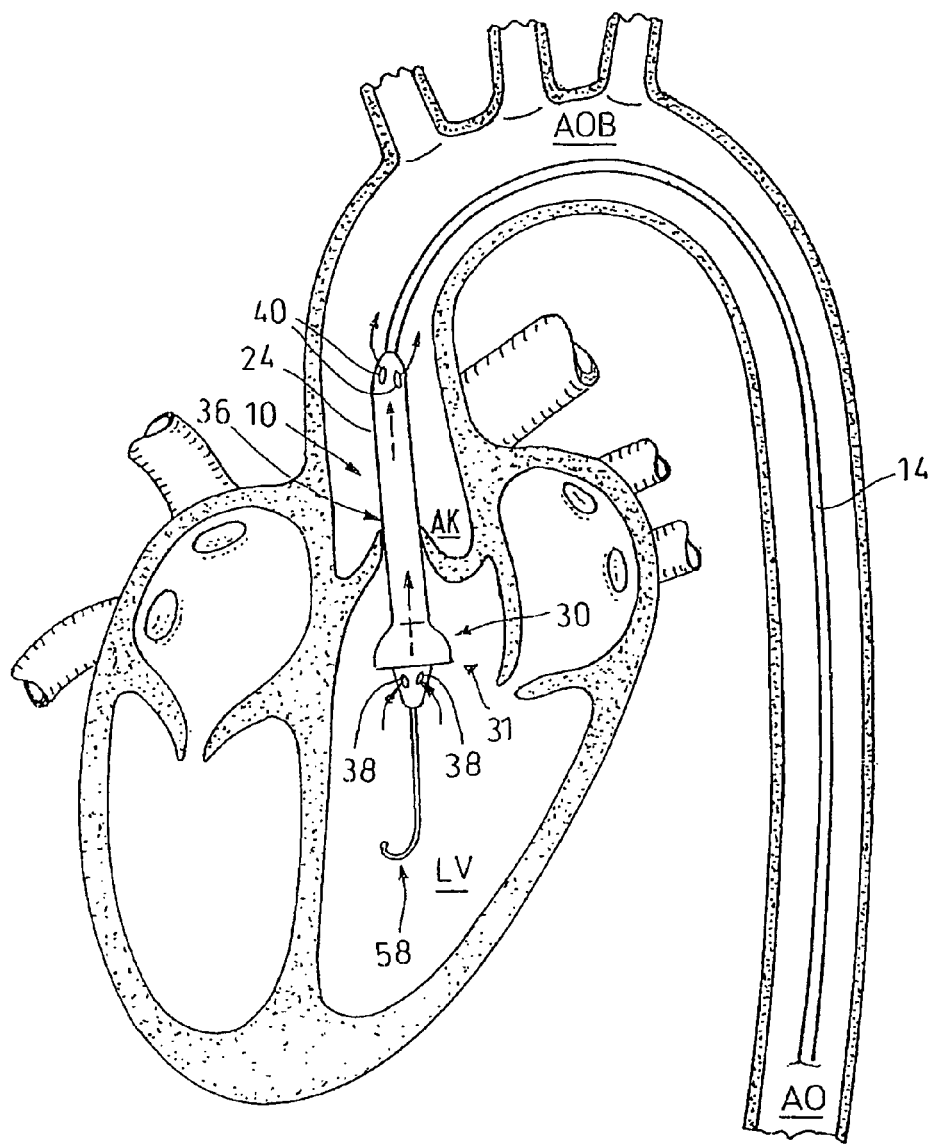
FIG. 10 shows a first embodiment of the blood pump in a human heart.

The blood pump 10 comprises an elongate flexible bendable shaft 12 included in a catheter 14. The catheter 14 is defined by a flexible tube with a diameter of approximately 2 mm. The catheter 14 is preferably made of an abrasion-resistant polymer, such as polyamide or polyurethane. The flexible shaft 12 extends through the catheter 14. The shaft is conventionally defined by a multi-file wire bundle and can be made hollow for accepting a central guide wire 56, if desired. Shaft 12 is driven at its proximal end by a motor not shown, e.g. at 5,000 to 15,000 rpm, while the catheter 14 is retained in place. At the distal end, i.e. the left end in FIG. 1, the shaft 12 comprises a rigid portion 16. The distal end of the catheter 14 is connected with the shaft via a sliding bearing 18. An impeller 20 is fastened to the rigid portion 16 of the shaft 12 via hinges 22 such that the impeller is foldable against the shaft 12. The impeller 20 and a distal portion of the shaft 12 and the catheter 14 are enclosed by an envelope 24. The envelope 24 is preferably made of a sack-like polyurethane skin. The material properties of polyurethane allow a good connection between the envelope 24 and the catheter 14. The distal end of the envelope 24 comprises a hub 26 in which the distal end 28 of the shaft 12 is supported. The shaft cannot be axially displaced but is adapted to rotate in the hub 26 such that the envelope 24 is secured against rotation with the rotating shaft 12.

The envelope 24 comprises an annular bulge 30 in the region of the impeller 20, the impeller 20 rotating in said bulge. The distal portion of the envelope 24 comprising the bulge 30 and the impeller 20 defines a pump head 31. In the distal region of the bulge 30 the envelope 24 comprises a concentric planar wall 32 which is arranged at a small distance to the distal side of the impeller 20. The bulge 30 is reinforced and stretched by concentrically arranged elastic bars 34. The distal ends of the bars 34 are connected with the planar wall 32. The proximal ends of the bars 34 are connected with the catheter 14. At the proximal side of the bulge 30 the envelope 24 comprises an elongate cylindrical extension 36. The outer diameter of the cylindrical extension 36 is smaller than the that of the bulge 30. In the distal and the proximal region the envelope 24 comprises rear and front flow openings 38,40. In the embodiment shown in FIG. 1, the front flow opening 38 is an inlet opening, and the rear flow opening 40 is an outlet opening. Between the radially outer end of the impeller 20 and the envelope 24 an annular deflection channel 42 is defined during operation of the blood pump, through which deflection channel the radially delivered blood flows and is deflected towards the shaft.

The impeller 20 comprises two essentially parallel supporting walls 44 and 46 which are permanently connected, at a distance of 2 mm, for example, with the rigid portion 16 of the shaft 12 via hinges 22. Each supporting wall 44,46 is defined by six spokes 48. The angle between respective adjacent spokes 48 is approximately 60°. The spokes 48 define a respective spoke wheel which is covered with a polymer skin 50. The spokes 48 and the polymer skin 50 define a respective supporting wall. The outer contour of the two supporting walls 44,46 is circular and has an outer diameter of approximately 10 mm. Alternatively, as shown in FIG. 3 by a dot-dash line, the outer edge of the side walls between the spokes 48 may be deformed an define an polygonal course. The polymer skin 50 of the front supporting wall 44 comprises a circular opening 52 enclosing the rigid portion 16 of the shaft 12. The opening 52 has an outer diameter of approximately 5 mm. The polymer skin 50 of the rear supporting wall 46 extends continuously from the rigid portion 16 of the shaft 12 to the outer radial end of the supporting wall 46.

Between the supporting walls 44, 46 radial vanes 54 are arranged in the region of the polymer skin 50 of the front supporting wall 44, which vanes extend perpendicularly to the supporting walls 44,46. The vanes 54 are sails of a polymer skin tied between the supporting walls 44,46. The radius of the rear supporting wall 46 is slightly smaller than the radius of the front supporting wall 44. In the operating condition of the pump, the front supporting wall 44 is arranged at a small distance of approximately 1 mm to the envelope 24. The radially outer edge of the rear supporting wall 46 is disposed at a larger distance to the envelope 24. Thus, a deflection channel 42 is defined through which the blood can flow, while the small distance of approximately 0.1 mm between the front supporting wall 44 and the envelope 24 allows only a comparably small amount of blood to flow. An undesired return flow of blood is thus prevented. The principle of the radially delivering impeller 20 allows for larger structural tolerances of the blood pump and makes the blood pump itself unsusceptible to misalignments.

In the operating condition of the first embodiment of the blood pump 10 shown in FIG. 1 the blood of the essentially axially directed blood flow passes through the front flow openings 38 of the envelope 24 and into the blood pump 10.

The main directions of the blood flow are indicated by the arrows in FIG. 1. The blood flows from the flow openings 38 through the opening 52 in the front supporting wall 44 and into the impeller 20. The impeller 20 is placed into rotation by the rotating shaft 12 driven by a motor not shown. The continuous rear supporting wall 46 deflects the incoming and essentially axially directed blood flow such that it defines a radial blood flow inside the impeller 20, the radial blood flow being directed towards the vanes 54. In doing so, the rotational movement of the shaft 12 is transmitted from the rigid portion 16 of the shaft via the hinges 22 to the spokes 48 and finally to the vanes 54. Due to the rotational movement of the impeller 20 the vanes 54 spin the blood in radially outward direction. The radially outward directed blood flow in the impeller is increased by the delivering action of the vanes 54. The blood spun in radially outward direction impinges upon the flexible polymer skin of the envelope 24 in the region of the bulge 30 and is directed by the envelope 24 through the deflection channel 42. In the region of the deflection channel 42 the radial main direction of the blood flow is deflected towards the shaft 12 such that an axial swirling flow along the shaft 12 is produced. Due to the fact that the planar wall 32 of the envelope 24 closely bears upon the front supporting wall 44 at a distance of approximately 0.1 mm, virtually no blood can flow back between the supporting wall 44 and the planar wall 32.

The essentially funnel-shaped bulge 30 directs the blood accelerated by the impeller 20 into the cylindrical extension 36 of the envelope 24. In the cylindrical extension 36 the blood flow is again axially directed. The blood leaves the blood pump 10 through the rear flow opening 40. A typical flow rate obtained during practical application of the blood pump is approximately 2 to 5 liters per minute. For delivering this quantity, the radial pump requires a relatively low speed of approximately 5,000 to 15,000 rpm. In the radial pump according to the invention the dimensions of the regions through which the blood flows may be selected such that damage to the blood is prevented to a large extent.

The blood pump is intravascularly moved forward, typically through the aorta of the left ventricle. For this purpose, first the outer diameter of the blood pump of approximately 10 mm must be reduced by folding. The flexible structure of the blood pump allows for simple folding as shown in FIG. 5. Here, the arrows indicate the direction of movement during the folding process. By relative displacement of the shaft 12 and the catheter 14, e.g. by moving the catheter 14 forward from the rear end to beyond the shaft 12, the impeller 20 is folded towards the shaft 12 by the envelope 24 and the bars 34. The supporting walls 44, 46 are folded against the shaft at the hinges 22, wherein the polymer skins 50 between the spokes 48 and the flexible vanes 54 are folded together. The spokes 48 are folded against the shaft 12, wherein the spokes of the rear supporting wall 46, which are offset relative to the spokes of the front supporting wall 44, bear upon the shaft in the spaces between the spokes of the front supporting wall 44. Due to the offset arrangement of the spokes 48 of the front and the rear supporting wall the blood pump has a small outer diameter of approximately 3 mm in the folded condition. The blood pump 10 is intravascularly inserted in the folded condition. For inserting the blood pump through the skin and tissue into the blood vessel, the catheter 14 is included in an insertable tube not shown. Retracting the catheter 14 into the insertable tube allows the blood pump 10 to be folded as well.

The blood pump is unfolded as follows: for operating the blood pump 10 the shaft 12 is placed into rotation by the motor not shown. Thereby centrifugal forces act upon the impeller 20 which rotates with the shaft 12. These centrifugal forces cause the impeller 20 to unfold at the hinges 22. The radially outer ends of the impeller 20 press from the inside against the envelope 24 and automatically unfold the latter. The blood pressed by the impeller 20 against the envelope 24 lends a stable and taut structure to the envelope 24 since the pressure inside the envelope is higher than that of the environment. As an alternative to the illustrated methodology of unfolding, an active unfolding of the impeller takes place starting from the hinges 22 since the supporting structure 48,22 of the impeller 20 is made of a superelastic metal alloy and is of the self-unfolding type which is later radially stabilized by rotation.

FIG. 6 shows an alternative embodiment of the blood pump 10. The envelope 24 does not comprise a concentric planar wall in the region of the bulge 30. The impeller 20 does not radially perpendicularly extend from the shaft 12 when the shaft 12 rotates for operating the pump 10, but extends such that it defines a taper angle $\alpha$ between the supporting walls 44,46 and the shaft 12. The angle $\alpha$ is smaller than 90°. Here it amounts to approximately 70°. During rotation of the shaft 12 and the rigid portion 16 of the shaft the impeller 20 is automatically raised by the centrifugal forces acting upon the impeller until the angle $\alpha$ reaches its maximum value at the operating condition. The rotating front supporting wall 44 of the impeller 20 is pressed against the envelope 24. Between the front supporting wall 44 and the envelope 24 a channel 60 is defined in the region of the bulge 30, said channel being kept sufficiently small by rotation of the impeller 20 for keeping a return flow of the blood through the channel 60 as small as possible. The pumping action of the blood pump is effective from the distal end to the proximal end. The inclined position of the two supporting walls 44,46 of the impeller 20 facilitates folding of the impeller 20 by relative axial displacement of the shaft 12 and the catheter 14. FIG. 6 shows a guide wire 56 extending through the shaft 12, the end 58 of said guide wire being "J"-shaped, wherein the blood pump 10 can be inserted into the heart via said guide wire. Before operation, the guide wire 56 is removed.

FIG. 7 shows another embodiment of the blood pump 10, which differs from the embodiment shown in FIG. 6 in that the impeller 20 extends from the shaft at angle $\alpha$ of more than 90°. Here the angle $\alpha$ amounts to approximately 110°. Thus the blood flows in the reverse direction in the blood pump 10 as compared with FIG. 6. The pumping action is effective from the proximal end to the distal end. The blood flows through the rear flow opening 40 into the blood pump 10 and leaves the blood pump 10 through the front flow openings 38. In the embodiment shown in FIG. 7, the impeller 20 is foldable in the opposite direction, i.e. towards the distal, i.e. the left end of the shaft 12 as shown in FIG. 7. Depending on the folding direction of the impeller 20, the blood pump 10 may deliver in forward direction, i.e. from the distal end to the proximal end as shown in FIG. 6, or—e.g. for supporting the right ventricle—in rearward direction, i.e. from the proximal end to the distal end as shown in FIG. 7.

FIG. 8 shows an embodiment of the blood pump 10, wherein, as compared to the blood pump shown in FIG. 6, a partition wall 62 is additionally arranged immediately proximal to the rear supporting wall 46. The partition wall 62 is preferably made of a polymer skin whose radial inner end is permanently connected with the catheter 14 and whose radial outer end is permanently connected with the envelope 24. In the region of the deflection channel 42 the partition wall is provided with flow openings 64 through which the blood accelerated by the vanes 54 of the impeller 20 can flow into the region proximal to the partition wall 62. Between the partition wall 62 and the rear supporting wall 46 of the impeller 20 an additional channel 60 is defined which keeps an undesired return flow of blood in the region proximal to the impeller at a low level. As shown in the top view of FIG. 9, the impeller 20 comprises two identical supporting walls 44, 46. The supporting walls 44, 46 are defined by spoke wheels comprising spokes 48. The spokes 48 of the two supporting walls 44, 46 are congruous. Between the spokes 48 no polymer skins are provided. Between the congruous spokes 48 of the two supporting wall 44, 46 the vanes 54 of sail-type polymer skins are arranged. In this embodiment of the blood pump 10, the function of the polymer skin 50 of the rear supporting wall 46 of the first embodiment is assumed by the partition wall 62. The structure and the technical setup of the blood pump 10 are thus further simplified. Here, too, the impeller 20, together with the envelope 24, can be folded towards the shaft 12 for the purpose of reducing the outer diameter of the blood pump 10 in order to allow for simple intravascular insertion of the blood pump.

Folding of the blood pumps shown in FIGS. 6-8 by relative displacement of the shaft 12 and the catheter 14 may be performed by moving the shaft 12 forward from the rear end in the catheter 14, for example. In doing so, the envelope 24 is stretched and pulled towards the shaft 12. The impeller 20 is folded towards the shaft 12 by the envelope 24.

Figure 11:
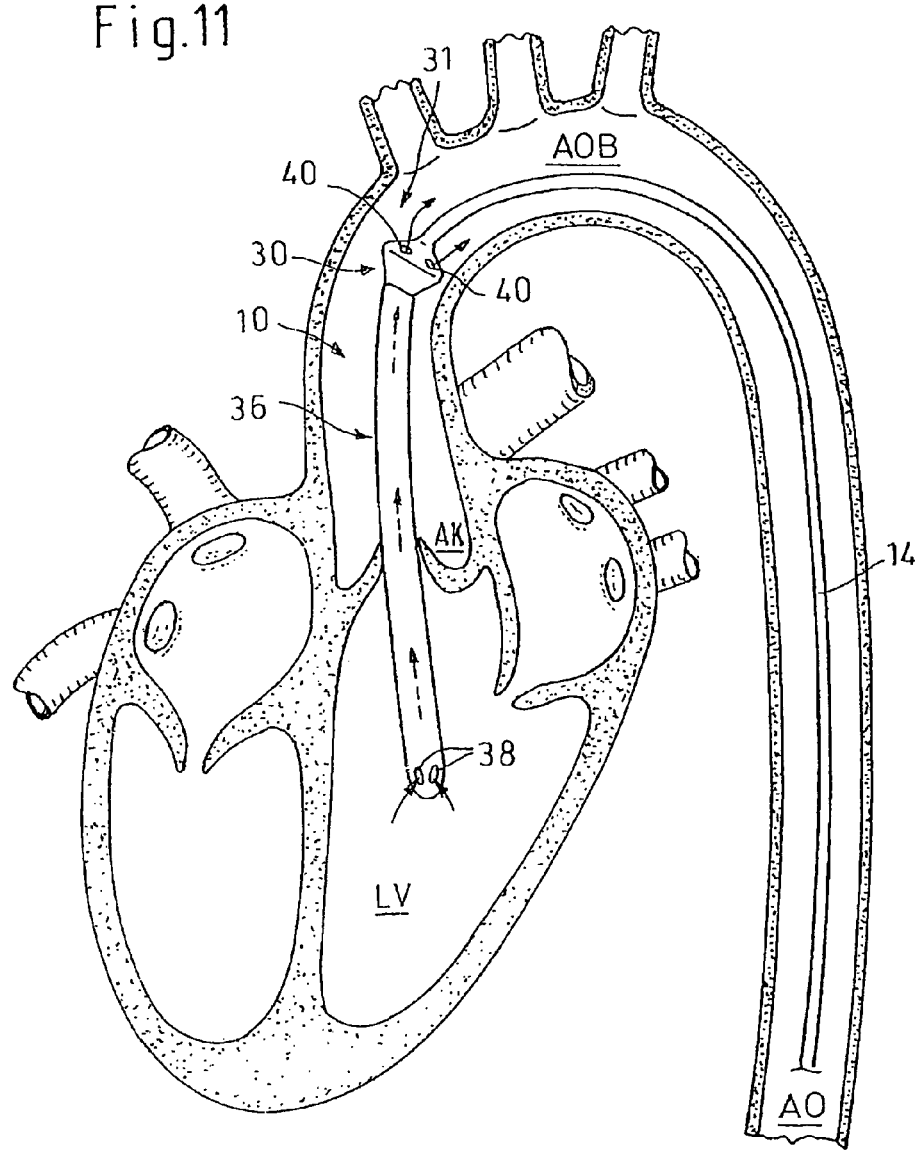
FIG. 11 shows a second embodiment of the blood pump in the human heart.
Figure 12:
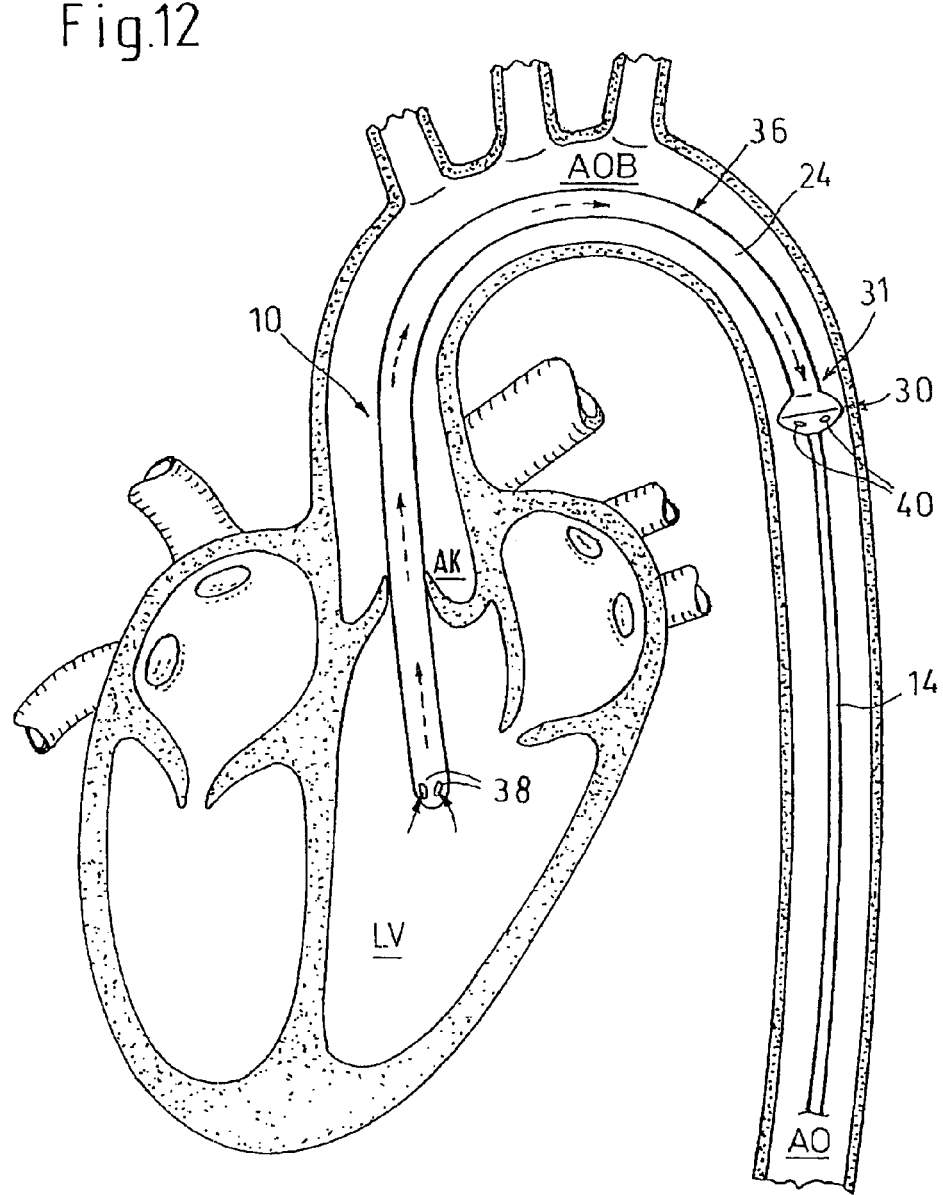
FIG. 12 shows a third embodiment of the blood pump in the human heart.

FIGS. 10-12 show different methods of placing the blood pump in the heart.

FIG. 10 shows the blood pump 10 according to the first embodiment of FIG. 1. The blood pump 10 is arranged such that the pump head 31 comprising the distally arranged flow openings 38 is located in the left ventricle LV, and the rear pump region comprising the proximally arranged flow openings 40 is located inside the aorta AO in front of the aortic arch AOB. The catheter 14 including the shaft 12 extends through the aorta AO and is bent in the region of the aortic arch AOB. The cylindrical extension 36 of the envelope 24 has a length of approximately 60 to 80 mm. The aortic valve AK surrounds the cylindrical extension 36. The blood pump 10 delivers the blood in forward direction from the distal end to the proximal end from the left ventricle LV into the aorta AO. The blood flows through the distal flow openings 38 into the envelope 24 of the blood pump 10. The rotating impeller accelerates the blood inside the bulge 30 of the envelope 24 and pumps the blood into the cylindrical extension 36 of the enclosure 24. The blood leaves the blood pump 10 through the proximal flow openings 40.

FIG. 10 shows an extension of the hard tip 26 in the form of a "pigtail" with the aid of which the blood pump 10 is supported at the myocardium for keeping a minimum distance between the suction region of the blood pump 10 and the inner wall of the myocardium.

FIG. 11 shows the method of placing a proximally arranged blood pump 10. The distal end of the blood pump comprising the flow openings 38 is located in the left ventricle LV inside the heart. The pump head 31 comprising the proximal flow openings 40 and the bulge 30 including the impeller 20 is located inside the aorta AO distally to the aortic arch AOB. The catheter 14 including the drive shaft 12 extends through the aortic arch AOB. In the region of the aortic arch AOB the flexible shaft 12 is bent. The aortic valve AK surrounds the cylindrical extension 36 of the blood pump envelope 24 arranged upstream as seen in the direction of delivery. The length of the cylindrical extension 36 is approximately 60 to 80 mm. The blood pump 10 delivers the blood in the same manner as the pump shown in FIG. 10, i.e. from the distal end to the proximal end from the left ventricle LV into the aorta AO. The blood enters into the cylindrical extension 36 of the blood pump envelope 24, the extension being located upstream and being radially reinforced as compared with the pump shown in FIG. 10, through the distal flow openings 38 and is taken in and accelerated by the impeller 20 not shown in the bulge 30 of the envelope 24. Inside the aorta AO and in front of the aortic arch AOB the accelerated blood flows out through the front flow openings 40.

FIG. 12 shows an embodiment of a blood pump 10 comprising an elongated cylindrical extension 36. The cylindrical extension 36 has a length of approximately 200 mm. The rear end of the blood pump 10 comprising the distal flow openings 38 is located in the left ventricle LV inside the heart. The upstream cylindrical extension 36 extends inside the aorta AO from the left ventricle LV through the aortic valves AK and the aortic arch AOB. Proximally to the aortic arch AOB the pump head 31 including the impeller 20 not shown inside the bulge 30 provided with the front flow openings 38 is located. Inside the left ventricle LV the blood enters into the blood pump 10 through the distal flow openings 38 and is taken in through the upstream cylindrical extension 36 and the aortic arch AOB, and leaves the blood pump 10 through the proximal flow openings 40 at a location proximal to the aortic arch AOB. The catheter 14 including the drive shaft 12 not shown extends inside the aorta AO but does not pass through the curvature of the aortic arch AOB. In this embodiment, the shaft 12 is bent to a lesser extent. The risk of damage to the shaft due to its being bent is thus reduced.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

What is claimed is:

1. A foldable intravascularly insertable blood pump comprising a rotor provided with vanes, a flexible shaft extending through a catheter and adapted to drive the rotor, and an envelope enclosing said rotor, wherein the rotor and vanes define an impeller which accelerates blood in a radial outward direction through centrifugal forces without any essential axial component, and the envelope comprises an annular bulge in a region of said impeller, wherein between radially outer ends of the vanes and the envelope an annular deflection channel is defined which deflects radial flow in an axial direction.

2. The blood pump according to claim 1, wherein the envelope is connected to the catheter and the impeller is fastened to the shaft via hinges such that the impeller and the envelope are foldable by relative displacement of the shaft and the catheter.

3. The blood pump according to claim 1, wherein the impeller comprises two essentially parallel supporting walls between which flexible sails define said vanes.

4. The blood pump according to claim 3, wherein at least one of the supporting walls comprises spokes.

5. The blood pump according to claim 3, wherein one supporting wall is a continuous wall and the other supporting wall comprises an opening formed therein that is disposed about the shaft.

6. The blood pump according to claim 3, wherein the supporting walls are fastened to the shaft by a hinge.

7. The blood pump according to claim 3, wherein both supporting walls comprise spokes which are offset relative to each other.

8. The blood pump according to claim 3, wherein the two supporting walls include congruent spokes.

9. The blood pump according to claim 1, wherein the envelope comprises a cylindrical extension having an end in which flow openings are provided.

10. The blood pump according to claim 1, wherein the envelope comprises a hub in which the shaft is supported in an axially non-displaceable manner.

11. The blood pump according to claim 1, wherein the shaft comprises a rigid portion at its distal end, the impeller being fastened to said rigid portion.

12. The blood pump according to claim 1, wherein the envelope comprises a planar wall which is concentrically arranged about said shaft and spaced a small distance apart from the impeller.

13. The blood pump according to claim 1, wherein the impeller is axially foldable relative to the shaft both distally and proximally.

14. The blood pump according to claim 1, wherein the envelope comprises, on one side of the impeller, a partition wall provided with a flow opening in a region of the deflection channel.

\* \* \* \* \*